US008859552B2

(12) United States Patent
Bhat et al.

(10) Patent No.: US 8,859,552 B2
(45) Date of Patent: Oct. 14, 2014

(54) METHODS OF UTILIZING ARYLPIPERAZINE DERIVATIVES

(71) Applicant: Reviva Pharmaceuticals, Inc., San Jose, CA (US)

(72) Inventors: Laxminarayan Bhat, Cupertino, CA (US); Prabhu Prasad Mohapatra, Logan, UT (US); Kouacou Adiey, San Jose, CA (US)

(73) Assignee: Reviva Pharmaceuticals, Inc., Santa Clara, CA (US)

( * ) Notice: Subject to any disclaimer, the term of this patent is extended or adjusted under 35 U.S.C. 154(b) by 0 days.

(21) Appl. No.: 13/914,424

(22) Filed: Jun. 10, 2013

(65) Prior Publication Data

US 2014/0155392 A1 Jun. 5, 2014

Related U.S. Application Data

(62) Division of application No. 13/465,549, filed on May 7, 2012, now Pat. No. 8,461,154, which is a division of application No. 12/714,406, filed on Feb. 26, 2010, now Pat. No. 8,188,076.

(60) Provisional application No. 61/155,791, filed on Feb. 26, 2009.

(51) Int. Cl.
| C07D 403/06 | (2006.01) |
| C07D 403/12 | (2006.01) |
| C07D 403/14 | (2006.01) |
| A61K 31/498 | (2006.01) |

(52) U.S. Cl.
USPC .......................................... 514/249; 544/354

(58) Field of Classification Search
USPC .......................................... 544/354; 514/249
See application file for complete search history.

(56) References Cited

U.S. PATENT DOCUMENTS

| 3,274,194 A | 9/1966 | Hayano |
| 3,770,734 A | 11/1973 | Pesson et al. |
| 3,845,770 A | 11/1974 | Theeuwes et al. |
| 3,879,393 A | 4/1975 | Havera |
| 3,916,899 A | 11/1975 | Theeuwes et al. |
| 4,455,422 A | 6/1984 | Banno et al. |
| 4,711,883 A | 12/1987 | Bandurco et al. |
| 4,803,203 A | 2/1989 | Caprathe et al. |
| 4,914,094 A | 4/1990 | Oshiro et al. |
| 4,977,166 A | 12/1990 | Hardy et al. |
| 5,112,598 A | 5/1992 | Biesalski |
| 5,234,924 A | 8/1993 | Taverne et al. |
| 5,308,844 A | 5/1994 | Rieu et al. |
| 5,556,611 A | 9/1996 | Biesalski |
| 5,698,155 A | 12/1997 | Grosswald et al. |
| 5,919,784 A | 7/1999 | Lesieur et al. |
| 5,994,542 A | 11/1999 | Asada et al. |
| 7,253,168 B2 | 8/2007 | Hutchison et al. |
| 2007/0031513 A1 | 2/2007 | Kikuchi et al. |
| 2008/0293736 A1 | 11/2008 | Bhat et al. |
| 2009/0298819 A1 | 12/2009 | Bhat et al. |
| 2010/0216783 A1 | 8/2010 | Bhat et al. |

FOREIGN PATENT DOCUMENTS

| BE | 745077 | 7/1970 |
| EP | 0161498 A1 | 11/1985 |
| JP | 59070675 | 4/1984 |
| JP | 60169467 A | 9/1985 |
| JP | 5331151 A | 12/1993 |
| JP | 2007137818 A | 6/2007 |
| WO | WO-9916751 | 8/1999 |
| WO | WO-03064393 | 8/2003 |
| WO | WO-2004063162 | 7/2004 |
| WO | WO-2004099152 | 11/2004 |
| WO | WO-2005092841 | 6/2005 |
| WO | WO-2006030446 | 3/2006 |
| WO | WO-2009154993 | 12/2009 |

OTHER PUBLICATIONS

Bamba, M. et al., "Release Mechanisms in Gelforming Sustained Release Preparations," International Journal of Pharmaceutics, 1979, pp. 307-315, vol. 2.
Cecchetti et al.: "(1,4-Benzothiazinyloxy)alkylpiperazine derivatives as potential antihypertensive agents", Bioorganic & Medicinal Chemistry Letters, Pergamon, Elsevier Science, GB, vol. 10, No. 5, Mar. 1, 2000, pp. 465-468.
Conley, R.R. et al., "Drug-Drug Interactions Associated with Second-Generation Antipsychotics: Considerations for Clinicians and Patients," Psychopharmacology Bulletin, 2007, pp. 77-97, vol. 40, No. 1.
Di Pietro, N.C. et al., "Dopamine and Serotonin Interactions in the Prefrontal Cortex: Insights on Antipsychotic Drugs and Their Mechanism of Action," Pharmacopsychiatry, 2007, pp. S27-S33, vol. 40, Suppl. 1.
During, M.J. et al., "Controlled Release of Dopamine from a Polymeric Brain Implant: In Vivo Characterization," Annals of Neurolology, Apr. 1989, pp. 351-356, vol. 25, No. 4.
Gundlach, A.L. et al., "$^{125}$I-Spiperone: A Novel Ligand for D.sub.2 Dopamine Receptors," Life Sciences, 1984, pp. 1984-1988, vol. 35.
Howard, M.A. et al., "Intracerebral Drug Delivery in Rats with Lesion-Induced Memory Deficits," J. Neurosurg., 1989, pp. 105-112, vol. 71.
Hoyer, D. et al., "Molecular Pharmacology of 5-HT$_1$ and 5-HT$_2$ Recognition Sites in Rat and Pig Brain Membranes: Radioligand Binding Studies with [$^3$H]5-HT, [$^3$H]8-OH-DPAT, (-)[$^{125}$I]Iodocyanopindolol, [$^3$H]Mesulergine and [$^3$H]Ketanserin," European Journal of Pharmacology, 1985, pp. 13-23, vol. 118.
Jarvie, K.R. et al., "Molecular Cloning, Stable Expression and Desensitization of the Human Dopamine D1B / D5 Receptor," Journal of Receptor Research, 1993, pp. 573-590, vol. 13 No. 1-4.

(Continued)

*Primary Examiner* — Kahsay Habte
(74) *Attorney, Agent, or Firm* — Perkins Coie LLP; Viola T. Kung

(57) ABSTRACT

The present invention provides arylpiperazine derivatives which can be advantageously used for treating schizophrenia and related psychoses such as acute manic, bipolar disorder, autistic disorder, and depression.

20 Claims, No Drawings

(56) References Cited

OTHER PUBLICATIONS

Langer, R. et al., "Chemical and Physical Structure of Polymers as Carriers for Controlled Release of Bioactive Agents: A Review," 1983, Journal of Macromolecular Science: Reviews in Macromolecular Chemistry and Physics, 1983, pp. 61-126, vol. 23, No. 1.

Langer, R., "New Methods of Drug Delivery," Science, Sep. 28, 1990, pp. 1527-1533, vol. 249.

Levy, R. et al., "Inhibition of Calcification of Bioprosthetic Heart Valves by Local Controlled-Release Diphosphonate," Science, Apr. 12, 1985, pp. 190-192, vol. 228, No. 4696.

Leysen, J.E. et al., "[$^3$H]Ketanserin (R 41 468), a Selective $^3$H-Ligand for Serotonin$_2$ Receptor Binding Sites," Molecular Pharmacology, 1982, pp. 301-314, vol. 21.

Martin, G.R. et al., "Receptors for 5-Hydroxytryptamine: Current Perspectives on Classification and Nomenclature," Neuropharmacology, 1994, pp. 261-273, vol. 33, No. 3/4.

Miyamoto, S. et al., "Treatments for Schizophrenia: A Critical Review of Pharmacology and Mechanisms of Action of Antipsychotic Drugs," Molecular Psychiatry, 2005, pp. 79-104, vol. 10.

Mulder, H. et al., "Prevalence of Patients Using Drugs Metabolized by Cytochrome P450 2D6 in Different Populations: a Cross-Sectional Study," The Annals of Pharmacotherapy, Mar. 2007, pp. 408-413, vol. 41, No. 3.

PCT International Search Report and Written Opinion, PCT Application No. PCT/US10/25687, Apr. 12, 2010, 7 pages.

PCT International Search Report and Written Opinion, PCT Application No. PCT/US10/25688, May 19, 2010, 9 pages.

Saudek, C.D. et al., "A Preliminary Trial of the Programmable Implantable Medication System for Insulation Delivery," The New England Journal of Medicine, Aug. 31, 1989, pp. 574-579, vol. 321, No. 9.

Schoeffter, P. et al., "How Selective is GR 43175? Interactions with Functional 5-HT$_{1A}$, 5-HT$_{1B}$, 5-HT$_{1C}$ and 5-HT$_{1D}$ Receptors," Naunyn-Schmiedeberg's Arch. Pharmac., 1989, pp. 135-138, vol. 340.

Sefton, M.V., "Implantable Pumps," CRC Critical Reviews in Biomedical Engineering, 1987, pp. 201-240, vol. 14, Issue 3.

Snyder, S.H., "A Complex in Psychosis," Nature, Mar. 6, 2008, pp. 38-39, vol. 452, Issue No. 7183.

Stark, A.D. et al., "Interaction of the Novel Antipsychotic Aripiprazole with 5-HT.sub.1A and 5-HT.sub.2A Receptors: Functional Receptor-Binding and In Vivo Electrophysiological Studies," Psychopharmacology 2007, 190, pp. 373-382.

Supplementary European Search Report dated Jun. 25, 2012 for Application No. EP10746949.

Verma, R.K. et al., "Osmotically Controlled Oral Drug Delivery," Drug Development and Industrial Pharmacy, 2000, pp. 695-708, vol. 26, No. 7.

METHODS OF UTILIZING ARYLPIPERAZINE DERIVATIVES

CROSS REFERENCE TO RELATED APPLICATIONS

This application is a divisional application of U.S. application Ser. No. 13/465,549, filed May 7, 2012; which is a divisional application of U.S. application Ser. No. 12/714,406, filed Feb. 26, 2010, now U.S. Pat. No. 8,188,076; which claims the benefit of U.S. Provisional Application No. 61/155,791, filed Feb. 26, 2009; the contents of the above applications are incorporated by reference in their entireties.

FIELD OF THE INVENTION

The present invention relates to compositions of arylpiperazine derivatives, synthesis of arylpiperazine derivatives, and methods of utilizing arylpiperazine derivatives. The present invention more particularly relates to synthesis, compositions and methods of utilizing arylpiperazine based compounds which are useful for the pharmacological treatment of schizophrenia and related psychoses such as acute manic, bipolar disorder, autistic disorder and depression.

BACKGROUND OF THE INVENTION

Medications used to treat psychotic disorders are called antipsychotics. Typical antipsychotics (sometimes referred to as conventional antipsychotics) are class of first generation antipsychotic drugs and used to treat psychosis including schizophrenia. The typical antipsychotics include chlorpromazine (THORAZINE®), fluphenazine (PROLIXIN®), haloperidol (HALDOL®), thiothixene (NAVANE®), trifluoroperazine (STELAZINE®), perphenazine (TRILAFON®), and thioridazine (MELLARIL®). The second generation antipsychotics introduced in the 1990's are called atypical antipsychotics. Compared to the first generation antipsychotics, the atypical antipsychotics appear to be equally effective in reducing the positive symptoms like hallucinations and delusions but may be better than the typical antipsychotics at relieving the negative symptoms of schizophrenia such as apathy, withdrawal, emotional depression and the like. The atypical antipsychotics currently in clinical use include Aripiprazole (ABILIFY®), clozapine (CLOZARIL®), risperidone (RISPERDAL®), olanzapine (ZYPREXA®), quetiapine (SEROQUEL®), and ziprasidone (GEODON®).

Atypical antipsychotics have diminished propensity to cause extrapyramidal symptoms (EPS) and tardive dyskinesia (TD) than typical antipsychotics. Additional benefits associated with the atypical antipsychotics include better treatment of negative symptoms, better compliance, possible benefits for cognitive impairments, and lower rates of relapse. Within the class of atypical antipsychotics, however, differences exist both in efficacy and side effects. Clozapine does not cause EPS, and is clearly more effective than all other antipsychotics used in humans to date. It is however a life-altering drug, because of its side effects and need for continual medical monitoring, in some countries, for agranulocytosis. This has markedly limited its use. The other atypical antipsychotics with the greatest amount of efficacy data are risperidone and olanzapine. These drugs are the most commonly used first-line antipsychotics today. This is warranted because they are more clinically effective than conventional drugs and much easier to use than clozapine. However, both risperidone and olanzapine are limited by side effects. Risperidone causes prolactin elevations, weight gain and dose-dependant EPS. Olanzapine use is associated with much more weight gain in addition to lipid and glucose abnormalities. Qetiapine and Ziprasidone may be safer alternatives to risperidone and olanzapine but these drugs do not appear to be as clinically effective as the other atypical antipsychotics. Aripiprazole is one of a new generation of atypical antipsychotic drugs approved by the FDA for the treatment of schizophrenia in November 2002 (Satyanarayana, C. et al. WO 2006/030446; Tsujimori, H. et al. WO 2004/063162; Salama, P. et al. WO 2004/099152; Wikstorm, H. et al. WO 2003/064393). It was approved for the treatment of acute mania and mixed episode associated with bipolar disorder in March 2005. Aripiprazole does not differ greatly from other atypical antipsychotics with respect to treatment response, efficacy and tolerability.

Atypical antipsychotics are increasingly being used in children and adolescents for a variety of psychiatric conditions. Conditions for which atypical antipsychotics are prescribed include bipolar disorder, psychotic depression, schizophrenia, pervasive developmental disorders, attention-deficit/hyperactivity disorder (ADHD), oppositional defiant disorder (ODD), and conduct disorder. They are also used symptomatically to treat rage, insomnia, and anorexia. Younger patients appear to be at a higher risk of adverse effects associated with the treatment of atypical antipsychotics especially weight gain and drug induced diabetes mellitus.

In general, atypical antipsychotics share many of the side effects of typical antipsychotics, including sedation, akathisia, weight gain, extrapyramidal symptoms (EPS), neuromalignant syndrome, and tardive dyskinesia; longer experience with them have shown that new risks need to be considered, such as metabolic syndromes and QTc prolongation. QTc prolongation is known to have potential liability to produce fatal cardiac arrhythmias of Torsades de Pointes (TdP). Drug induced adverse metabolic effects such as weight gain, lipid abnormalities, and diabetes mellitus have been identified as a major risk factor for various medical disorders that might be responsible for some of the increased morbidity and mortality rates in psychotic patients treated with atypical antipsychotics.

Off-target pharmacology and drug to drug interactions are mainly responsible for most of the adverse side effects associated with the atypical antipsychotics. All the atypical antipsychotic drugs currently being used for the treatment of schizophrenia and related psychotic disorders have poor therapeutic target selectivity. For example, one of the most widely prescribed atypical antipsychotic drugs, Olanzapine and the most effective atypical antipsychotic drug, clozapine are reported to have significant activities against more than 12 receptors such as dopamine ($D_1$, $D_2$, $D_3$ and $D_4$), serotonin ($5-HT_{2A}$, $5-HT_{2C}$, $5-HT_6$, and $5-HT_7$), adrenergic (alpha 1 and alpha 2), histamine ($H_1$), muscarinic ($M_1$), Dopamine transporter (DAT) and norepinephrine transporter (NET) receptors (Miyamoto et al., Molecular Psychiatry, 2005, 10, 79). Similarly, the other FDA approved atypical antipsychotics such as risperidone and aripiprazole are also reported to have significant activities against more than nine of the receptors mentioned above. The current research suggests that compounds exhibiting activity against dopamine ($D_2$) and serotonin ($5-HT_{1A}$ and $5-HT_{2A}$) receptors may have the intended antipsychotic effect (Snyder, S. H., Nature 2008, 452, 38-39; Di Pietro, N. C., Seamans, J. K., Pharmacopsychitry 2007, 40(S1), S27-S33; Stark, A. D. et al., Psychopharmacology 2007, 190, 373-382) while compounds exhibiting activity against other receptors like serotonin, $5HT_{2C}$, histamine ($H_1$), and adrenergic (alpha 1) may cause adverse side effects such as cardiac arrhythmias.

Although, the atypical antipsychotics (aripiprazole, clozapine, risperidone, olanzapine, quetiapine, and ziprasidone) currently in clinical use represent significant advances in treatment of people with schizophrenia, there is a need for new psychotropic drugs with improved safety profiles.

Therefore, development of a novel antipsychotic that has improved therapeutic target selectivity than the currently available therapies would provide effective and safer medicines for the treatment of schizophrenia and related psychotic disorders.

SUMMARY OF THE INVENTION

The present invention provides compounds, synthesis of the compounds, compositions and methods of using the compounds for treating schizophrenia and related psychoses such as acute manic, bipolar disorder, autistic disorder and depression, where the compounds are arylpiperazine derivatives. The present invention provides methods for synthesizing such arylpiperazine compounds. The present invention also provides methods for using arylpiperazine based atypical antipsychotics, and composition of arylpiperazine based atypical antipsychotics for treating schizophrenia and related psychoses such as acute manic, bipolar disorder, autistic disorder and depression.

The compounds of the subject invention provide next generation novel antipsychotics that are particularly effective and safer for the treatment of schizophrenia. They are advantageous because of their highly desirable pharmacological, metabolic, and pharmacokinetics profiles. The compounds of the invention are designed:

1) to exhibit affinity for dopamine 2 ($D_2$) receptor;
2) to exhibit affinity for serotonin 1A ($5-HT_{1A}$) receptor;
3) to exhibit affinity for serotonin 2A ($5-HT_{2A}$) receptors
4) to form therapeutically inactive or least active metabolite(s).

In one aspect, the present invention provides arylpiperazine derivatives comprising compounds of Formula (1):

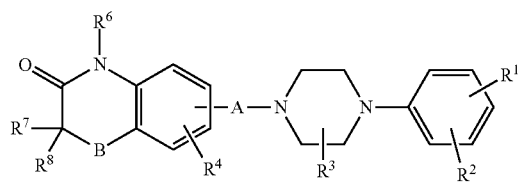

Formula 1 wherein:
A is $-(CH_2)_n-$, $-O-(CH_2)_n-$, $-S-(CH_2)_n-$, $-S(O)(O)-(CH_2)_n-$, $-NH-(CH_2)_n-$, $-CH_2-O-(CH_2)_n-$, $-(CH_2)_n-O-CH_2-CH_2-$, $-CH_2-S-(CH_2)_n-$, $-(CH_2)_n-S-CH_2-CH_2-$, $-CH_2-S(O)(O)-(CH_2)_n-$, $-(CH_2)_n-S(O)(O)-CH_2-CH_2-$, $-O-C(O)-(CH_2)_n-$, $-S-C(O)-(CH_2)_n-$, $-NH-C(O)-(CH_2)_n-$, $-CH_2-C(O)-O-(CH_2)_n-$, $-CH_2-C(O)-NH-(CH_2)_n-$, $-CH_2-C(O)-S-(CH_2)_n-$, $-(CH_2)_n-C(O)-O-CH_2-CH_2-$, $-(CH_2)_n-C(O)-NH-CH_2-CH_2-$, $-(CH_2)_n-C(O)-S-CH_2-CH_2-$, $-CH_2-O-C(O)-(CH_2)_n-$, $-CH_2-NH-C(O)-(CH_2)_n-$, $-CH_2-S-C(O)-(CH_2)_n-$, $-(CH_2)_n-O-C(O)-CH_2-CH_2-$, $(CH_2)_n-NH-C(O)-CH_2-CH_2-$, or $(CH_2)_n-S-C(O)-CH_2-CH_2-$, wherein n is an integer from 1 to 7;

B is O, S, S(O)(O), or $NR^5$; and
each of $R^1$, $R^2$, $R^3$, $R^4$, $R^5$, $R^6$, $R^7$, and $R^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylasulfinyl, alkylsulfonyl, alkylthio, amino, alkylamino, arylalkylamino, dialkkylamino, arylalkoxy, arylalkoxycarbonylalkoxy, arylalkoxycarbonylalkylamino, aryloxycarbonyl, arylloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein $R^1$, $R^2$, $R^3$, $R^4$, $R^5$, $R^6$, $R^7$ and $R^8$ and A may optionally be substituted with isotopes that include, but not limited to $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$;

or a pharmaceutically acceptable salt, racemate or diastereomeric mixtures thereof.

In one aspect of the invention, pharmaceutical compositions are provided comprising the compounds of the present disclosure.

In one aspect of the invention, methods of treating one of psychoses, schizophrenia, acute mania, bipolar disorder, autistic disorder or depression are described, comprising administering to a patient in need thereof the compounds of the present disclosure.

In one aspect of the invention, compounds of the present disclosure are used to treat psychoses, schizophrenia, acute mania, bipolar disorder, autistic disorder or depression.

In one aspect of the invention, compounds of present disclosure are used in the manufacture of a medicament for use in the treatment of psychoses, schizophrenia, acute mania, bipolar disorder, autistic disorder or depression treat psychoses, schizophrenia, acute mania, bipolar disorder, autistic disorder or depression.

DETAILED DESCRIPTION OF THE INVENTION

The present invention relates to synthesis, compositions and methods of using arylpiperazine derivatives which are useful for treating schizophrenia and related psychoses such as acute manic, bipolar disorder, autistic disorder and depression. The present invention provides compounds, compositions and methods for pharmacological treatment of schizophrenia and related psychoses such as acute manic, bipolar disorder, autistic disorder, and depression.

Definitions

Unless otherwise stated, the following terms used in this application, including the specification and claims, have the definitions given below. Any terms not directly defined herein shall be understood to have the meanings commonly associated with them as understood within the art of the present disclosure.

It must be noted that, as used in the specification and the appended claims, the singular forms "a," "an" and "the" include plural referents unless the context clearly dictates otherwise.

Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences,* 18$^{th}$ Edition (Easton, Pennsylvania: Mack Publishing Company, 1990).

"Compounds of the invention" refers to compounds encompassed by structural Formula (1) as disclosed herein. The compounds of the invention can be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2$H, $^3$H, $^{13}$C, $^{15}$N, $^{18}$O, $^{17}$O, $^{31}$P, $^{32}$P, $^{35}$S, $^{18}$F and a $^{36}$Cl. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered in isolated form, which means separated from a synthetic organic reaction mixture.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl (allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-prop an-1-yl, 2-methyl-propan-2-yl, cyclobutan-1-yl, but-1-en-1-yl, but-1-en-2-yl, 2-methyl-prop-1-en-1-yl, but-2-en-2-yl, but-2-en-2-yl, buta-1,3-dien-1-yl buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien 1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O) OCR'R"OC(O)R''', where R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$OC(O)CH$_3$, —C(O) OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O) OCR'R"C(O)R''', where R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —C(O)OCH$_2$C(O)CH$_3$, —C(O) OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R''', where R, R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$OC(O) CH$_3$, —NHC(O)OCH$_2$OC(O)CH$_2$CH$_3$, —NHC(O)OCH (CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R''', where R, R', R", and R''' are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "amide" as defined herein.

"Alkylamino" means a radical —NHR where R represents an alkyl, or cycloalkyl group as defined herein that may be optionally substituted by one or more substituents as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted by one or more substituents as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted by one or more substituents as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted by one or more substituents as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted by one or more substituents as defined herein. Representative examples include, but are not limited to methylthio, ethylthio, propylthio, butylthio, and the like.

"Amide" or "acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, formylamino acetylamino, cyclohexylcarbonylamino, cyclohexylmethylcarbonyl-amino, benzoylamino, benzylcarbonylamino and the like.

"Amino" refers to the radical —NH$_2$.

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is (C$_6$-C$_{30}$)arylalkyl, e.g., the alkanyl, alkenyl or alkynyl moiety of the arylalkyl group is (C$_1$-C$_{10}$) and the aryl moiety is (C$_6$-C$_{20}$), more preferably, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylalkoxy" refers to an —O-arylalkyl radical where arylalkyl is as defined herein that may be optionally substituted by one or more substituents as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OCH$_2$C$_6$H$_5$, —OCH(CH$_3$)C(O)OCH$_2$C$_6$H$_5$, —OCH(C$_6$H$_5$)C(O)OCH$_2$C$_6$H$_5$, —OCH(CH$_2$C$_6$H$_5$)C(O)OCH$_2$C$_6$H$_5$, —OC(CH$_3$)(CH$_3$)C(O)OCH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted by one or more substituents as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)NRR where each R group is independently, hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cylic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is (C$_3$-C$_{10}$) cycloalkyl, more preferably (C$_3$-C$_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein that may be optionally substituted by one or more substituents as defined herein.

"Dialkylamino" means a radical —NRR' where R and R' independently represent an alkyl or cycloalkyl group as defined herein that may be optionally substituted by one or more substituents as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to be derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein that may be optionally substituted by one or more substituents as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Ether" refers to a radical —OR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Halo" means fluoro, chloro, bromo, or iodo.

"Heteroalkoxy" means an —O-heteroalkyl radical where heteroalkyl is as defined herein that may be optionally substituted by one or more substituents as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR'—, =N—N=, —N=N—, —N=N—NR'—, —PH—, —P(O)$_2$—, —O—P(O)—, —S(O—, —S(O)$_2$—, —SnH$_2$—, and the like, wherein R' is hydrogen, alkyl, substituted alkyl, cycloalkyl, substituted cycloalkyl, aryl or substituted aryl that may be optionally substituted by one or more substituents as defined herein.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined that may be optionally substituted by one or more substituents as defined herein.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Phosphonate" refers to a radical —P(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Preventing" or "Prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a group of atoms that when attached to a reactive group in a molecule masks, reduces or prevents that reactivity. Examples of protecting groups can be found in Green et al., "Protective Groups in Organic Chemistry", (Wiley, $2^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxy-carbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Substituted" refers to a group in which one or more hydrogen atoms are each independently replaced with the same or different substituents(s). Typical substituents include, but are not limited to, —X, —$R^{54}$, —O$^-$, =O, —O$R^{54}$, —S$R^{54}$, —S, =S, —N$R^{54}R^{55}$, =N$R^{54}$, —C$X_3$, —C$F_3$, —CN, —OCN, —SCN, —NO, —N$O_2$, =$N_2$, —$N_3$, —S(O)$_2$O$^-$, —S(O)$_2$OH, —S(O)$_2$O$R^{54}$, —OS(O)$_2$O$^{31}$, —OS(O)$_2R^{54}$, —P(O)(O—)$_2$, —P(O)(O$R^{14}$)(O$^{31}$), —OP(O)(O$R^{54}$)(O$R^{55}$), —C(O)$R^{54}$, —C(S)$R^{54}$, —C(O)O$R^{54}$, —C(O)N$R^{54}R^{55}$, —C(O)O$^-$, —C(S)O$R^{54}$, —N$R^{56}$C(O)N$R^{54}R^{55}$, N$R^{56}$C(S) N$R^{54}R^{55}$, —N$R^{57}$C(N$R^{56}$)N$R^{54}R^{55}$, and —C(N$R^{56}$) N$R^{54}R^{55}$, where each X is independently a halogen; each $R^{54}$, $R^{55}$, $R^{56}$ and $R^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —N$R^{58}R^{59}$, —C(O)$R^{58}$ or —S(O)$_2R^{58}$ or optionally $R^{58}$ and $R^{59}$ together with the atom to which they are both attached form a cycloheteroalkyl or substituted cycloheteroalkyl ring; and $R^{58}$ and $R^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonamide" refers to a radical —S(O)(O)NR'R", where R' and R" are independently hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein or optionally R' and R" together with the atom to which they are both attached form a cycloheteroalkyl or substituted cycloheteroalkyl ring. Representative examples include but not limited to azetidinyl, pyrrolidinyl, piperidinyl, morpholinyl, 4-(NR''')-piperazinyl or imidazolyl group wherein said group may be optionally substituted by one or more substituents as defined herein. R''' hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Sulfonate" refers to a radical —S(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Thio" means the radical —SH.

"Thioether" refers to a radical —SR, where R is alkyl, cycloalkyl, cycloheteroalkyl, aryl, arylalkyl, heteroalkyl, heteroaryl, heteroarylalkyl, as defined herein that may be optionally substituted by one or more substituents as defined herein.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Compounds of the Invention

In one aspect of the present invention, compounds of Formula (1) are described:

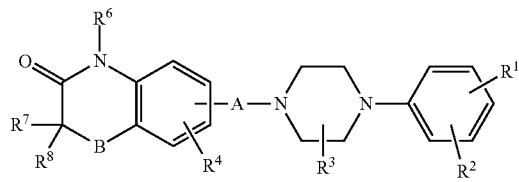

Formula 1 wherein:
A is —(CH$_2$)$_n$—, —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, or (CH$_2$)$_n$—S—C(O)—CH$_2$—CH$_2$—, wherein n is an integer from 1 to 7;

B is O, S, S(O)(O), or NR$^5$; and each of R$^1$, R$^2$, R$^3$, R$^4$, R$^5$, R$^6$, R$^7$, and R$^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonylalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein R$^1$, R$^2$, R$^3$, R$^4$, R$^5$, R$^6$, R$^7$ and R$^8$ and A may optionally be substituted with isotopes that include, but not limited to $^2$H (deuterium), $^3$H (tritium), $^{13}$C, $^{36}$Cl, $^{18}$F, $^{15}$N, $^{17}$O, $^{18}$O, $^{31}$P, $^{32}$P, and $^{35}$S;

or a pharmaceutically acceptable salt, racemate or diastereomeric mixtures thereof.

In another aspect, compounds of Formula (1a) are described:

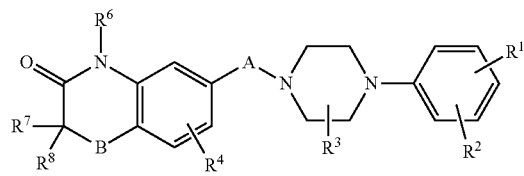

Formula Ia wherein:
A is —(CH$_2$)$_n$—, —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, or (CH$_2$)$_n$—S—C(O)—CH$_2$—CH$_2$—, wherein n is an integer from 1 to 7;

B is O, S, S(O)(O), or NR$^5$; and each of $R^1$, $R^2$, $R^3$, $R^4$, $R^5$, $R^6$, $R^7$, and $R^8$ is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonyllalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halo, heteroaryloxycarbonyl, hydroxy, phosphate, phosphonate, sulfate, sulfonate, or sulfonamide, wherein $R^1$, $R^2$, $R^3$, $R^4$, $R^5$, $R^6$, $R^7$ and $R^8$ and A may optionally be substituted with isotopes that include, but not limited to $^2H$ (deuterium), $^3H$ (tritium), $^{13}C$, $^{36}Cl$, $^{18}F$, $^{15}N$, $^{17}O$, $^{18}O$, $^{31}P$, $^{32}P$, and $^{35}S$;

or a pharmaceutically acceptable salt, racemate or diastereomeric mixtures thereof.

In another aspect of the invention, A is $-(CH_2)_n-$.

In another aspect of the invention, A is $-O-(CH_2)_n-$, $-S-(CH_2)_n-$, $-CH_2-O-(CH_2)_n-$, $-(CH_2)_n-O-CH_2-CH_2-$, $-CH_2-S-(CH_2)_n-$, or $-(CH_2)_n-S-CH_2-CH_2-$.

In another aspect of the invention, A is $-NH-C(O)-(CH_2)_n-$, $-CH_2-NH-C(O)-(CH_2)_n-$, $-CH_2-C(O)-NH-(CH_2)_n-$ or $-(CH_2)_n-C(O)-NH-CH_2-CH_2-$.

In another aspect of the invention, B is O.

In another aspect of the invention, $R^4$ is H.

In another aspect of the invention, each of $R^1$ and $R^2$ is independently H, halogen, haloalkyl or alkoxy.

The compounds of this invention described herein can have one or more of the following characteristics or properties:

(a) Compounds of the invention can have affinity for dopamine $D_2$ receptors;

(b) Compounds of the invention can have affinity for serotonin 5-$HT_{1A}$ receptors;

(c) Compounds of the invention can have affinity for serotonin 5-$HT_{2A}$ receptors;

(d) The primary metabolite(s), regardless of the electrophysiological properties of the parent drug, has, or have, negligible inhibitory activity at the HERG (human ether-a-go-go related gene) potassium channel at the normal therapeutic concentration of the parent drug in plasma (e.g. the concentration of the metabolite must be at least five times higher than the normal therapeutic concentration of the parent compound before activity at the HERG potassium channel is observed);

(e) Compounds of the invention, as well as the metabolites thereof, do not cause, or have reduced incidence of metabolic drug-drug interaction (DDI) when co-administered with other drugs;

(f) Compounds of the invention, as well as metabolites thereof, do not substantially elevate liver function test (LFT) values when administered alone;

(g) Oral bioavailability of the compounds is consistent with oral administration using standard pharmacological oral formulations; however, the compounds, and compositions thereof, can also be administered using any delivery system that produces constant and controllable blood levels overt time.

In one aspect, the invention provides compounds having any two or more of the above-identified characteristics or properties. In another aspect, the invention provides for compounds having at least any three or more of the above-identified properties or characteristics. Preferably, the compounds of the invention have all seven characteristics or properties.

Additional modifications of the compounds disclosed herein can readily be made by those skilled in the art. Thus, analogs and salts of the exemplified compounds are within the scope of the subject invention. With knowledge of the compounds of the subject invention skilled artisans can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. Thus, for example, the compounds are at least about 90% enantiomeric excess, preferably at least about 95% enantiomeric excess, more preferably at least about 97% enantiomeric excess., or even more preferably, at least 99% or greater than 99% enantiomeric excess.

Synthesis of the Compounds of the Invention

The compounds of the invention can be obtained via the synthetic methods illustrated in Schemes 1-2. Several methods have been described in the art for the synthesis of arylpiperazine derivatives. The starting materials and building blocks useful for preparing compounds of the invention and intermediates thereof are commercially available or can be prepared by well-known synthetic methods (see e.g., Green et al., "Protective Groups in Organic Chemistry,"(Wiley, 4th ed., 2006); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, $4^{th}$ ed., 1991; Larock "Comprehensive Organic Transformations," Wiley-VCH Publishers, $2^{nd}$ ed., 19991 Paquette, "Encyclopedia of Reagents for Organic Synthesis," John Wiley and Sons, $1^{st}$ ed., 1995). Other methods for the synthesis of arylpiperazine derivatives described herein are either described in the art or will be readily apparent to the skilled artisan in view of the references provided above and may be used to synthesize the compounds of the invention. Accordingly, the methods presented in the Schemes herein are illustrative rather than comprehensive.

In one method arylpiperazine derivatives comprising Formula (1) was prepared as described in Scheme 1. The starting building block 6-nitrobenzoxazinone 1 was purchased from the commercial source Sigma-Aldrich. The compound 1 can also be synthesized from a method well known in the literature. The reduction of nitro moiety in compound 1 using a reducing agent like potassium borohydride (KBH4) in presence of a mild Lewis acid copper (1) chloride (CuCl) in a protic solvent such as methanol gave 6-aminobenzoxazinone 2. The target benzoxazinone 4 was prepared by coupling the amine 2 with a suitable carboxylic acid 3 under standard coupling conditions using dicyclohexylcarbodiimde (DCC) as coupling agent in presence of a mild base 4-(N,N,-dimethylamino)pyridine (DMAP) in a polar aprotic solvent medium. The carboxylic acid 3 was prepared by the alkylation of a suitable arylpiperazine with an appropriate bromocarboxylic acid ester followed by saponification. The benzoxazinone derivative 4 was converted into hydrochloride salt 5 by treating with hydrogen chloride under standard conditions. The benzoxazinones 4 can also be converted into other form of pharmaceutically acceptable salts such as methanesulfonic acid salts and lower aliphatic carboxylic acid salts using well known methods in the field.

carbonate ($K_2CO_3$) to give the ester 8. The ester 8 was treated with aluminum chloride ($AlCl_3$) in anhydrous dichloromethane at reflux temperature to get the corresponding nitrophenol derivative 9. The compound 11 was prepared by alkylating the nitrophenol 9 with 1,4-dibromobutane 10 under identical reaction conditions described for preparing the compound 8 (Scheme 2). The reaction of compound 11 with arylpiperazine 12 in presence of N,N-diisopropylethylamine (DIEA) in acetonitrile at approximately 60-70° C. for 8 to 16 h gave the compound 13. The compound 13 when subjected to reduction conditions using iron (III) chloride in presence of metallic iron in ethanol and acetic acid solvent mixture at reflux temperature afforded the corresponding benzoxazinone 14 which was converted into hydrochloride salt 15 by treating with hydrogen chloride under standard conditions. Other standard nitro group reduction conditions Scheme 1

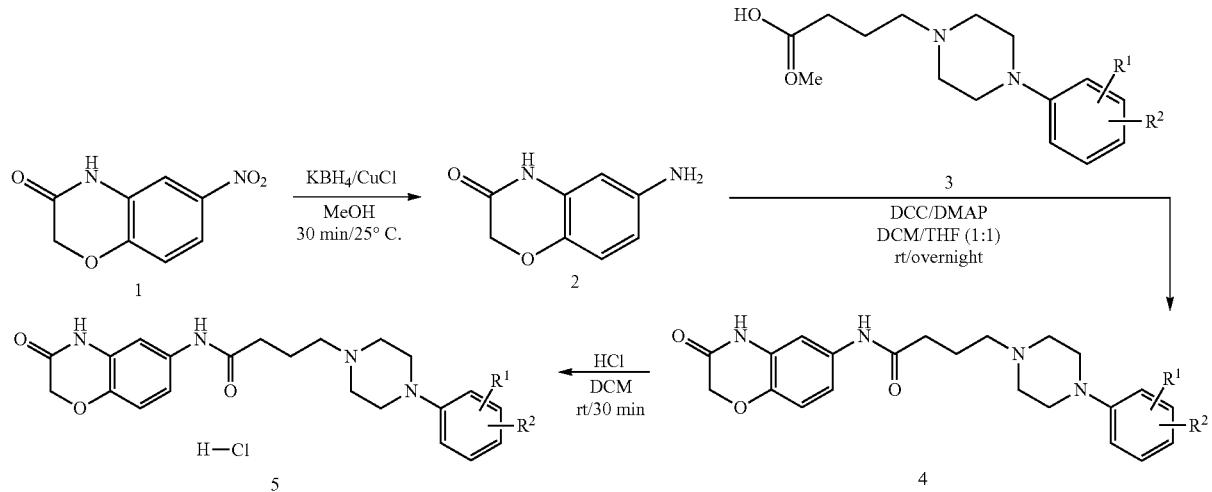

a) $R^1$ = 2-OMe, $R^2$ = H;
b) $R^1$ = 2-Cl, $R^2$ = 3-Cl

In another method, arylpiperazine derivatives comprising Formula (1) were prepared as described in Scheme 2. The starting building block 4-methoxy-2-nitrophenol 6 was purchased from the commercial source Sigma-Aldrich. The nitrophenol 6 was alkylated with ethylbromoacetate 7 by heating in acetone in presence of a mild base potassium like hydrogenation in presence of catalyst palladium on activated carbon (Pd/C) also gave corresponding cyclized product 14. The benzoxazinones 14 can also be converted into other form of pharmaceutically acceptable salts such as methanesulfonic acid salts and lower aliphatic carboxylic acid salts using well known methods in the field.

Scheme 2

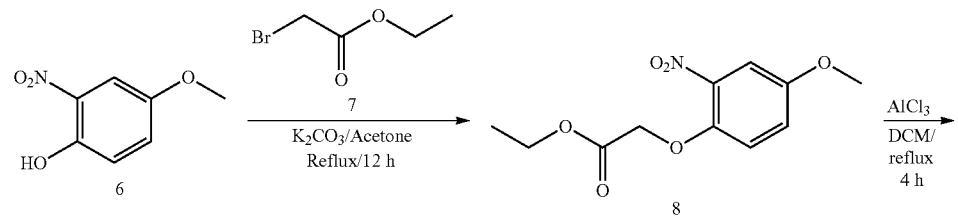

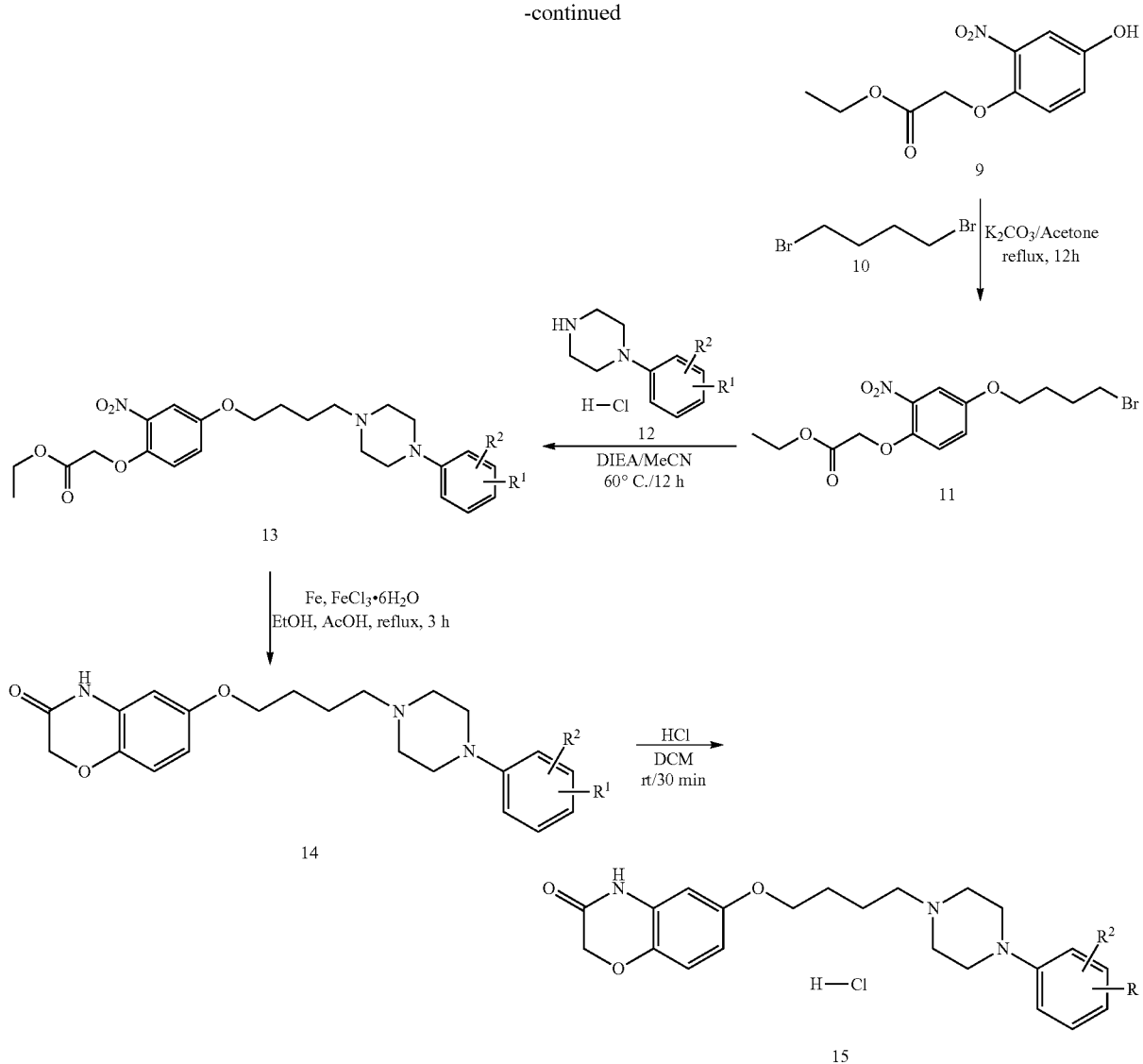

Therapeutic Uses of Compounds of Structural Formula (1)

The present invention relates to synthesis, compositions and methods of using arylpiperazine based compounds which are useful for treating schizophrenia and related psychoses such as acute maniac, bipolar disorder, autistic disorder and depression. The present invention provides methods for synthesizing such arylpiperazine based antipsychotic agents. The present invention also provides methods for using arylpiperazine based antipsychotic agents and composition of arylpiperazine based antipsychotic agents for treating schizophrenia and related psychoses such as acute maniac, bipolar disorder, autistic disorder and depression.

In accordance with the invention, a compound and/or a composition containing a compound of structural Formula (1) is administered to a patient, preferably a human, suffering from schizoprenia. Further, in certain embodiments, the compounds and/or compositions of the invention are administered to a patient, preferably a human, as a treatment or preventive measure against acute manic, bipolar disorder, autistic disorder and depression.

Thus, those of skill in the art may readily assay and use the compounds and/or compositions containing compound(s) of structural Formula (1) to treat a medical condition for which an antipsychotic is desired.

Therapeutic/Prophylactic Administration

The compounds, and/or compositions containing compounds(s), of structural Formula (1) can be advantageously used in human medicine. As previously described in detail above, compounds and compositions containing compound(s) of structural Formula (1) are useful for the treatment of schizophrenia and related psychoses such as acute manic, bipolar disorder, autistic disorder and depression.

When used to treat or prevent the above disease or disorders compounds and/or compositions of the invention can be administered or applied singly, in combination with other agents. The compounds and/or compositions of the invention can also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985; , Science 228:190; During et al., 1989, Ann Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethers have been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formula (1) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

Compositions of the Invention

In one aspect of the invention, pharmaceutical compositions are provided comprising the compounds of the present disclosure.

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, $17^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcamitines and the like may be added.

Compositions for administration via other routes may also be contemplated. For buccal administration, the compositions may take the form of tablets, lozenges, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

Methods of Use and Doses

A compound of the invention, or compositions thereof, will generally be used in an amount effective to achieve the intended purpose. For use to treat schizophrenia and related psychoses such as acute manic, bipolar disorder, autistic disorder and depression. The compounds of Formula (1) and compositions containing a compound of Formula (1) are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day, and more preferably, once per day. Dosing may be repeated intermittently, may be provided alone or in combination with other drugs and may continue as long as required for effective treatment of the disease state or disorder.

The compounds and/or compositions containing compound(s), of structural Formula (1) for the pharmacological treatment of schizophrenia and related psychoses such as acute maniac, bipolar disorder, autistic disorder and depression may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 10 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

In one aspect of the invention, methods of treating one of psychoses, schizophrenia, acute mania, bipolar disorder, autistic disorder or depression are described, comprising administering to a patient in need thereof the compounds the present disclosure.

In another aspect of the invention, the method treats schizophrenia.

In another aspect of the invention, the method treats bipolar disorder.

In one aspect of the invention, compounds of the present disclosure used to treat psychoses, schizophrenia, acute mania, bipolar disorder, autistic disorder or depression.

In another aspect of the invention, the use comprises the treatment of schizophrenia.

In another aspect of the invention, the use comprises the treatment of bipolar disorder.

In one aspect of the invention, compounds of the present disclosure are used in the manufacture of a medicament for use in the treatment of psychoses, schizophrenia, acute mania, bipolar disorder, autistic disorder or depression treat psychoses, schizophrenia, acute mania, bipolar disorder, autistic disorder or depression.

In another aspect of the invention, the use is for the treatment of schizophrenia.

In another aspect of the invention, the use is for the treatment of bipolar disorder.

Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, composition comprising a compound of the invention is administered concurrently with the administration of another therapeutic agent, which can be part of the same composition. In another embodiment, a composition comprising a compound of the invention is administered prior or subsequent to administration of another therapeutic agent.

EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.
Atm=Atmosphere
CDI=1,1'-Carbonyldiimidazole
DCM=dichloromethane
DMAP=4-N,N-dimethylaminopyridine
DMF=N,N-dimethylformamide
g=gram
h=hours
L=liter
LC/MS=liquid chromatography/mass spectroscopy
M=molar
mL=milliliter
mmol=millimols
nM=nanomolar
µM=micromolar
MTBE=methyl tert-butyl ether
rt=room temperature
TEA=triethylamine
THF=tetrahydrofuran
TFA=trifluoroacetic acid Example 1

6-Amino-2H-benzo[b][1,4]oxazin-3(4H)-one (2) (Scheme 1). To a suspension of 6-nitro-2H-1,4-benzoxazin-3(4H)-one 1 (0.5 g, 0.0026 mol) and CuCl (0.77 g, 0.0078 mol) in anhydrous methanol (25 mL), stirred at 25° C. was added potassium borohydride (0.98 g, 0.018 mol) in portions (exothermic with evolution of hydrogen gas). The reaction mixture was stirred at 25° C. for 30 min. The black precipitate formed was filtered and washed with methanol. The combined filtrate and washings was evaporated to give 6-amino-2H-benzo[b][1,4]oxazin-3(4H)-one which was purified by silica gel column chromatography using ethyl acetate. Brown solid (0.29 g, 67%). $^1$H NMR (400 MHz, CDCl$_3$): δ 4.34 (s, 2H); 4.81 (s, 2H); 6.09 (dd, J=2.8, 8.4 Hz, 1H); 6.14 (d, J=2.8 Hz, 1H); 6.59 (d, J=8.4 Hz, 1H); 10.44 (s, 1H).

Example 2

4-(4-(2-Methoxyphenyl)piperazin-1-yl)-N-(3-oxo-3,4-dihydro-2H-benzo[b][1,4]oxazin-6-yl)butanamide (4a) (Scheme 1). A mixture of 6-amino-2H-benzo[b][1,4]oxazin-3(4H)-one 2 (0.08 g, 0.0005 mol), 4-(4-(substituted-phenyl)piperazin-1-yl)butanoic acid 3a (0.0005 mol), dicyclohexylcarbodiimide (0.1 g, 0.0005 mol), 4-(dimethylamino)pyridine (0.006 g, 0.00005 mol) in 10 mL dichloromethane was stirred at room temperature for overnight. The progress of the reaction was monitored by thin layer chromatography (TLC). The reaction mixture was cooled; filtered to remove the urea precipitated, washed with saturated sodium bicarbonate solution, dried over sodium sulfate and evaporated under reduced pressure to give 4-(4-(substituted-phenyl)piperazin-1-yl)-N-(3-oxo-3,4-dihydro-2H-benzo[b][1,4]oxazin-6-yl)butanamide 4a which was purified by silica gel column chromatography using 0-10% gradient of ethyl acetate and methanol. The pure product 4a gave satisfactory 1H NMR and/or Mass spectral data. White solid (0.06 g, 29%). $^1$H NMR (400 MHz, CDCl$_3$): δ 1.94-2.00 (m, 2H); 2.53-2.59 (m, 4H); 2.70 (br s, 4H); 3.14 (br s, 4H); 3.87 (s, 3H); 4.55 (s, 2H); 6.63 (dd, J=2.4, 8.8 Hz, 1H); 6.84-6.88 (m, 2H); 6.93-6.95 (m, 2H); 6.99-7.04 (m, 1H); 7.82 (d, J=2.4 Hz, 1H); 9.04 (br s, 1H); 9.12 (br s, 1H). MS (ESI): m/z=425.2 (M+H$^+$).

Example 3

4-(4-(2,3-Dichlorophenyl)piperazin-1-yl)-N-(3-oxo-3,4-dihydro-2H-benzo[b][1,4]oxazin-6-yl)butanamide (4b) (Scheme 1). The compound 4b was synthesized using the protocol described for the synthesis of compound 4a in Example 2 (Scheme 1). White solid (0.08 g, 34%). $^1$H NMR (400 MHz, CDCl$_3$): δ 1.93-2.00 (m, 2H); 2.50-2.57 (m, 4H); 2.68 (br s, 4H); 3.09 (br s, 4H); 4.50 (s, 2H); 6.63 (dd, J=2.4, 8.8 Hz, 1H); 6.88 (d, J=8.8 Hz; 1H); 6.99-6.92 (m, 1H); 7.13-7.20 (m, 2H); 7.71-7.72 (m, 1H); 8.46 (br s, 1H); 8.58 (br s, 1H). MS (ESI): m/z=463.2 (M$^+$).

Example 4

4-(4-(2-Methoxyphenyl)piperazin-1-yl)-N-(3-oxo-3,4-dihydro-2H-benzo[b][1,4]oxazin-6-yl)butanamide hydrochloride (5a) (Scheme 1). To a solution of 4-(4-(substituted-phenyl)piperazin-1-yl)-N-(3-oxo-3,4-dihydro-2H-benzo[b][1,4]oxazin-6-yl)butanamide 4a in 5 mL dichloromethane was added 2 mL 2M HCl solution in diethyl ether, and then the solution was evaporated at 25° C. to give 4-(4-(substituted-phenyl)piperazin-1-yl)-N-(3-oxo-3,4-dihydro-2H-benzo[b][1,4]oxazin-6-yl)butanamide hydrochloride 5a. The pure products 5a gave satisfactory 1H NMR and/or Mass spectral data. White solid (60 mg). MS (ESI): m/z=425.2 (M-HCl).

Example 5

4-(4-(2,3-Dichlorophenyl)piperazin-1-yl)-N-(3-oxo-3,4-dihydro-2H-benzo[b][1,4]oxazin-6-yl)butanamide hydrochloride (5b) (Scheme 1). The compound 5b was synthesized using the protocol described for the synthesis of compound 5a in Example 4 (Scheme 1). White solid (40 mg). MS (ESI): m/z=463.2 (M-HCl).

Example 6

Ethyl 2-(4-methoxy-2-nitrophenoxy)acetate (8) (Scheme 2). A mixture of 4-methoxy-2-nitrophenol 6 (1.69 g, 0.01 mol), potassium carbonate (2.76 g, 0.02 mol) and ethyl bromoacetate 7 (1.1 mL, 0.01 mol) in 20 mL anhydrous acetone was refluxed for overnight (12 h). The progress of the reaction was monitored by thin layer chromatography. The reaction mixture was evaporated, the residue was diluted with water and the mixture was extracted with ethyl acetate. The organic layer was washed with brine, dried over sodium sulfate and evaporated to give ethyl 2-(4-methoxy-2-nitrophenoxy)acetate 8 which was purified by silica gel column chromatography using 0-50% gradient of hexane and ethyl acetate. Yellow solid (2.18 g, 85%). $^1$H NMR (400 MHz, CDCl$_3$): δ 1.28 (t, J=7.2 Hz, 3H); 3.82 (s, 3H); 4.25 (q, J=7.2 Hz, 2H); 4.70 (s, 2H); 7.01 (d, J=9.2 Hz, 1H); 7.08 (dd, J=3.2, 9.2 Hz, 1H); 7.40 (d, J=2.8 Hz, 1H).

Example 7

Ethyl 2-(4-hydroxy-2-nitrophenoxy)acetate (9) (Scheme 2). To a solution of ethyl 2-(4-methoxy-2-nitrophenoxy)acetate 8 (1.0 g, 0.004 mol) in 10 mL dichloromethane cooled in an ice-bath was added aluminum chloride (1.6 g, 0.0133 mol) portion wise. The resulting mixture was gradually warmed to room temperature and then refluxed for 4 h. The progress of the reaction was monitored by thin layer chromatography (TLC). The reaction mixture was washed with saturated sodium bicarbonate solution and dried over sodium sulfate to give ethyl 2-(4-hydroxy-2-nitrophenoxy)acetate 9 which was purified by silica gel column chromatography using a gradient of hexane and ethyl acetate. White solid (0.28 g, 37%). $^1$H NMR (400 MHz, CDCl$_3$): δ 1.26 (t, J=6.8 Hz, 3H); 4.27 (q, J=6.8 Hz, 2H); 4.71 (S, 2H); 6.32 (S, 1H); 6.90 (d, J=8.8 Hz, 1H); 6.99 (dd, J=3.2 Hz; 8.8 Hz, 1H); 7.30 (d, J=2.8 Hz, 1H).

Example 8

Ethyl 2-(4-(4-bromobutoxy)-2-nitrophenoxy)acetate (11) (Scheme 2). To a solution of ethyl 2-(4-hydroxy-2-nitrophenoxy)acetate 9 (0.17 g, 0.0007 mol) in 10 mL acetone was added potassium carbonate (0.39 g, 0.0028 mol). The reaction mixture was stirred at room temperature for 10 min. Then 1,4-dibromobutane 10 (0.33 mL, 0.0028 mol) was added. The resulting mixture was heated at reflux for 12 h. The progress of the reaction was monitored by thin layer chromatography (TLC). Acetone was evaporated and the residue was diluted with water, extracted with ethyl acetate and dried over sodium sulfate to give ethyl 2-(4-(4-bromobutoxy)-2-nitrophenoxy)acetate 11 which was purified by silica gel column chromatography using 0-20% gradient of hexane and ethyl acetate. Yellow oil (0.52 g, 92%). $^1$H NMR (400 MHz, CDCl$_3$): δ 1.26 (t, J=6.8 Hz, 3H); 1.91-1.98 (m, 2H); 2.02-2.09 (m, 2H); 3.48 (t, J=6.8 Hz, 2H); 3.99 (t, J=6.0 Hz, 2H); 4.26 (q, J=6.8 Hz, 2H); 4.70 (s, 2H); 6.99-7.02 (m, 2H); 7.38 (d, J=3.2 Hz, 1H).

Example 9

Ethyl 2-(4-(4-(4-(2-methoxyphenyl)piperazin-1-yl)butoxy)-2-nitrophenoxy)acetate 13a (Scheme 2). A mixture of ethyl 2-(4-(4-bromobutoxy)-2-nitrophenoxy)acetate 11 (0.0007 mol), 1-(2-substituted-phenyl)piperazine hydrochloride 12 (0.16 g, 0.0007 mol), N,N-diisopropylethylamine (0.36 mL, 0.0021 mol) in 10 mL acetonitrile was heated at 60° C. for 12 h. The progress of the reaction was monitored by thin layer chromatography (TLC). The reaction mixture was evaporated to remove the volatiles and the residue was diluted with water, extracted with ethyl acetate, the organic extracts were washed with sodium bicarbonate solution and dried over sodium sulfate to give ethyl 2-(4-(4-(4-(substituted-phenyl)piperazin-1-yl)butoxy)-2-nitrophenoxy)acetate 13a which was purified by silica gel column chromatography using a gradient of hexane and ethyl acetate. The pure product 13a gave satisfactory 1H NMR and/or Mass spectral data. Colorless oil (0.3.g, 88%). $^1$H NMR (400 MHz, CDCl$_3$): δ 1.26 (t, J=6.8 Hz, 3H); 1.70-1.72 (m, 2H); 1.82-1.85 (m, 2H); 2.47 (t, J=6.4 Hz, 2H); 2.67 (br s, 4H); 3.10 (br s, 4H); 3.86 (s, 3H); 3.98 (t, J=6.4 Hz, 2H); 4.24 (q, J=6.8 Hz, 2H); 4.70 (s, 2H); 6.84-6.96-7.08 (m, 6H); 7.38 (d, J=2.8 Hz, 1H).

Example 10

Ethyl 2-(4-(4-(4-(2,3-dichlorophenyl)piperazin-1-yl)butoxy)-2-nitrophenoxy)acetate 13b (Scheme 2). The compound 13b was prepared using the protocol described for the synthesis of compound 13a as described in Example 9 (Scheme 2). Yellow oil (0.3 g, 81%). $^1$H NMR (400 MHz, CDCl$_3$): δ 1.26 (t, J=6.8 Hz, 3H); 1.70-1.73 (m, 2H); 1.80-1.85 (m, 2H); 2.48 (t, J=6.4 Hz, 2H); 2.65 (br s, 4H); 3.07 (br s, 4H); 3.99 (t, J=6.4 Hz, 2H); 4.26 (q, J=6.8 Hz, 2H); 4.70 (s, 2H); 6.94-7.08 (m, 3H); 7.13-7.16 (m, 2H); 7.39 (d, J=3.2 Hz, 1H).

Example 11

6-(4-(4-(2-methoxyphenyl)piperazin-1-yl)butoxy)-2H-benzo[b][1,4]oxazin-3(4H)-one (14a) (Scheme 2). Ethyl 2-(4-(4-(4-(substituted-phenyl)piperazin-1-yl)butoxy)-2-nitrophenoxy)acetate 13a (0.1 g, 0.0002 mol) was dissolved in a mixture of 10 mL ethanol and 1.2 mL acetic acid in a 100 mL flask equipped with an efficient condenser, and the stirred mixture brought to a gentle reflux. Iron powder (0.084 g, 0.0015 mol) was added, followed immediately by iron(III) chloride hexahydrate (0.01 g, 0.000034 mol). The mixture was refluxed for a further 3 h, then cooled and filtered using a Buchner funnel, washed with ethanol. The combined filtrate and washings were evaporated. To the residue was added ethyl acetate and water, and the aqueous layer was extracted twice with ethyl acetate. The combined organic layers were dried and concentrated to give 6-(4-(4-(substituted-phenyl)piperazin-1-yl)butoxy)-2H-benzo[b][1,4]oxazin-3(4H)-one 14a which was purified by silica gel column chromatography using a gradient of hexane and ethyl acetate. The pure product 14a gave satisfactory 1H NMR and/or Mass spectral data. Colorless oil (0.08 g, 97%). $^1$H NMR (400 MHz, CDCl$_3$): δ 1.70 (br s, 2H); 1.78 (br s, 2H); 2.47 (br s, 2H); 2.67 (br s, 4H); 3.10 (br s, 4H); 3.86 (s, 3H); 3.91 (br s, 2H); 4.55 (s, 2H); 6.38 (br s, 1H); 6-48-6.50 (m, 1H); 6.85-6.99 (m, 5H); 9.12 (br s, 1H). MS (ESI): m/z=412.3 (M$^+$+H).

Example 12

6-(4-(4-(2,3-dichlorophenyl)piperazin-1-yl)butoxy)-2H-benzo[b][1,4]oxazin-3(4H)-one (14b) (Scheme 2). The compound 14b was prepared using the protocol described for the synthesis of compound 14a as described in Example 11 (Scheme 2). Colorless oil (0.1 g, 42%). $^1$H NMR (400 MHz, CDCl$_3$): δ 1.79 (br s, 4H); 2.74 (br s, 2H); 2.96 (br s, 4H); 3.17 (br s, 4H); 3.91 (s, 2H); 4.05 (s, 2H); 6.44 (s, 1H); 6.48 (dd, J=2.4 Hz; 8.8 Hz, 1H); 6.85 (d, J=8.8 Hz, 1H); 6.96 (dd, J=2.0 Hz; 7.2 Hz, 1H); 7.12-7.19 (m, 2H); 9.49 (s, 1H); 9.87 (br s, 1H). MS (ESI): m/z=450.2 (M$^+$).

Example 13

6-(4-(4-(2-Methoxyphenyl)piperazin-1-yl)butoxy)-2H-benzo[b][1,4]oxazin-3(4H)-one hydrochloride (15a) (Scheme 2). To a solution of 6-(4-(4-(substituted-phenyl)piperazin-1-yl)butoxy)-2H-benzo[b][1,4]oxazin-3(4H)-one 14a in 5 mL dichloromethane was added 2 mL 2M HCl solution in diethyl ether, and then the solution was evaporated at 25° C. to give 6-(4-(4-(substituted-phenyl)piperazin-1-yl)butoxy)-

2H-benzo[b][1,4]oxazin-3(4H)-one hydrochloride 15a. The pure products 15a gave satisfactory 1H NMR and/or Mass spectral data. White solid (0.08 g). MS (ESI): m/z=412.3 (M-HCl).

Example 14

6-(4-(4-(2,3-Dichlorophenyl)piperazin-1-yl)butoxy)-2H-benzo[b][1,4]oxazin-3(4H)-one hydrochloride (15b) (Scheme 2). The compound 15b was prepared using the protocol described for the synthesis of compound 15a as described in Example 13 (Scheme 2). White solid (0.28 g). MS (ESI): m/z=450.2 (M-HCl).

In Vitro Pharmacology Results

The arylpiperazine derivatives comprising Formula (1) described in this invention were tested in the in vitro pharmacological assays to evaluate their activities for dopamine, $D_{2S}$, serotonin, $5\text{-HT}_{1A}$ and serotonin, $5\text{-HT}_{2A}$ receptors. The in vitro assay protocols and literature references are described herein.

Dopamine, $D_{2S}$ (human recombinant) binding assay
Materials and Methods:
Receptor Source: Human recombinant expressed in CHO cells
Radioligand: [$^3$H]Spiperone (20-60 Ci/mmol)
Control Compound: Haloperidol
Incubation Conditions: The reactions were carried out in 50 mM TRIS-HCl (pH 7.4) containing 120 mM NaCl, 5 mM KCl, 5 mM MgCl$_2$, 1 mM EDTA for 60 minutes at 25 C. The reaction was terminated by rapid vacuum filtration onto glass fiber filters. Radioactivity trapped onto the filters was determined and compared to control values in order to ascertain any interactions of test compounds with the cloned dopamine-$D_2$ short binding site (Literature Reference: Jarvis, K. R. et al. Journal of Receptor Research 1993, 13(1-4), 573-590; Gundlach, A. L. et al. Life Sciences 1984, 35, 1981-1988.)

Serotonin, $5\text{HT}_{1A}$ (human recombinant) binding assay
Materials and Methods:
Receptor Source: Human recombinant expressed in HEK-293 cells
Radioligand: [$^3$H]-8-OH-DPAT (221 Ci/mmol)
Control Compound: 8-OH-DPAT
Incubation Conditions: The reactions were carried out in 50 mM TRIS-HCl (pH 7.4) containing 10 mM MgSO$_4$, 0.5 mM EDTA and 0.1% Ascorbic acid at room temperature for 1 hour. The reaction was terminated by rapid vacuum filtration onto glass fiber filters. Radioactivity trapped onto the filters was determined and compared to control values in order to ascertain any interactions of test compounds with the cloned serotonin-$5\text{HT}_{1A}$ binding site (Literature Reference: Hoyer, D. et al. Eur. Journal Pharmacol. 1985, 118, 13-23; Schoeffter, P. and Hoyer, D. Naunyn-Schmiedeberg's Arch. Pharmac. 1989, 340, 135-138)

Serotonin, $5\text{HT}_{2A}$ (human) binding assay
Materials and Methods:
Receptor Source: Human Cortex
Radioligand: [$^3$H]-Ketanserin (60-90 Ci/mmol)
Control Compound: Ketanserin
Incubation Conditions: The reactions were carried out in 50 mM TRIS-HCl (pH 7.6) at room temperature for 90 minutes. The reaction was terminated by rapid vacuum filtration onto glass fiber filters. Radioactivity trapped onto the filters was determined and compared to control values in order to ascertain any interactions of test compounds with the serotonin-$5\text{HT}_{2A}$ binding site (Literature Reference: Leysen, J. E. et al. Mol. Pharmacol. 1982, 21, 301-314; Martin, G. R. and Humphrey, P. P. A. Neuropharmacol. 1994, 33(3/4), 261-273.)

The radioligand binding assays for dopamine-$D_{2S}$, serotonin-$5\text{HT}_{1A}$ and serotonin-$5\text{HT}_{2A}$ were carried out at six different concentrations and the test concentrations were 0.5 nM, 1 nM, 10 nm, 100 nM, 300 nM and 1000 nM.

The in vitro pharmacological activities of the selected compounds using radioligand binding assays are reported in the following table.

| Compound | Assay | IC50 | Ki |
|---|---|---|---|
| 15a (Example 13) | D2S | 0.98 nM | 0.30 nM |
| 15a (Example 13) | 5-HT1A | 0.97 nM | 0.65 nM |
| 15a (Example 13) | 5-HT2A | 262 nM | 118 nM |
| 15b (Example 14) | D2S | 1.96 nM | 0.61 nM |
| 15b (Example 14) | 5-HT1A | 2.25 nM | 1.50 nM |
| 15b (Example 14) | 5-HT2A | 130 nM | 58.50 nM |

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

What is claimed is:
1. A compound of Formula 1:

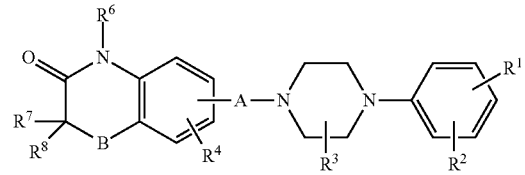

Formula 1 or a pharmaceutically acceptable salt, isomer, racemate, diastereomeric mixture thereof, wherein:

A is —(CH$_2$)$_n$—, —O—(CH$_2$)$_n$—, —S—(CH$_2$)$_n$—, —S(O)(O)—(CH$_2$)$_n$—, —NH—(CH$_2$)$_n$—, —CH$_2$—O—(CH$_2$)$_n$—, —(CH$_2$)$_n$—O—CH$_2$—CH$_2$—, —CH$_2$—S—(CH$_2$)$_n$—, —(CH$_2$)$_n$—S—CH$_2$—CH$_2$—, —CH$_2$—S(O)(O)—(CH$_2$)$_n$—, —(CH$_2$)$_n$—S(O)(O)—CH$_2$—CH$_2$—, —O—C(O)—(CH$_2$)$_n$—, —S—C(O)—(CH$_2$)$_n$—, —NH—C(O)—(CH$_2$)$_n$—, —CH$_2$—C(O)—O—(CH$_2$)$_n$—, —CH$_2$—C(O)—NH—(CH$_2$)$_n$—, —CH$_2$—C(O)—S—(CH$_2$)$_n$—, —(CH$_2$)$_n$—C(O)—O—CH$_2$—CH$_2$—, —(CH$_2$)$_n$—C(O)—NH—CH$_2$—CH$_2$—, —(CH$_2$)$_n$—C(O)—S—CH$_2$—CH$_2$—, —CH$_2$—O—C(O)—(CH$_2$)$_n$—, —CH$_2$—NH—C(O)—(CH$_2$)$_n$—, —CH$_2$—S—C(O)—(CH$_2$)$_n$—, —(CH$_2$)$_n$—O—C(O)—CH$_2$—CH$_2$—, (CH$_2$)$_n$—NH—C(O)—CH$_2$—CH$_2$—, or (CH$_2$)$_n$—S—C(O)—CH$_2$—CH$_2$—, wherein n is an integer from 1 to 7;

B is NR$^5$; and

R$^1$, R$^2$, R$^3$, R$^4$, R$^5$, R$^6$, R$^7$, and R$^8$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, acylalkyloxycarbonyl, acyloxyalkyloxycarbonyl, acylalkyloxycarbonylamino, acyloxyalkyloxycarbonylamino, alkoxy, alkoxycarbonyl, alkoxycarbonylalkoxy, alkoxycarbonylalkylamino, alkylsulfinyl, alkylsulfonyl, alkylthio, amino, alkylamino, arylalkylamino, dialkylamino, arylalkoxy, arylalkoxycarbonylalkoxy, arylalkoxycarbonylalkylamino, aryloxycarbonyl, aryloxycarbonylalkoxy, aryloxycarbonylalkylamino, carboxy, carbamoyl, carbamate, carbonate, cyano, halogen, heteroaryloxycarbonyl, hydroxy, phosphate, phosphonate, sulfate, sulfonate, or sulfonamide; wherein $R^1$, $R^2$, $R^3$, $R^4$, $R^6$, $R^7$ and $R^8$ and A are optionally substituted with isotopes selected from the group consisting of $^2$H (deuterium), $^3$H (tritium), $^{13}$C, $^{36}$Cl, $^{18}$F, $^{15}$N, $^{17}$O, $^{18}$O, $^{31}$P, $^{32}$P, and $^{35}$S.

2. The compound of claim 1, wherein the compound has Formula 1a:

Formula Ia

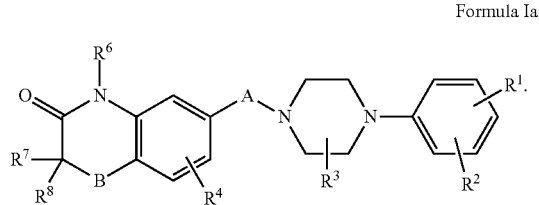

3. The compound of claim 1, wherein A is —O—$(CH_2)_n$—, —S—$(CH_2)_n$—, —$CH_2$—O—$(CH_2)_n$—, —$(CH_2)_n$—O—$CH_2$—$CH_2$—, —$CH_2$—S—$(CH_2)_n$—, or —$(CH_2)_n$—S—$CH_2$—$CH_2$—.

4. The compound of claim 1, wherein A is —NH—C(O)—$(CH_2)_n$—, —$CH_2$—NH—C(O)—$(CH_2)_n$—, —$CH_2$—C(O)—NH—$(CH_2)_n$— or —$(CH_2)_n$—C(O)—NH—$CH_2$—$CH_2$—.

5. The compound of claim 1, wherein A is —$(CH_2)_n$—.

6. The compound of claim 1, wherein $R^4$ is H.

7. The compound of claim 1, wherein $R^1$ and $R^2$ are independently H, halogen, or alkoxy.

8. The compound of claim 7, wherein $R^1$ is H, and $R^2$ is methoxy.

9. The compound of claim 1, wherein $R^1$ and $R^2$ are chloro.

10. The compound of claim 7, wherein A is —O—$(CH_2)_n$—; and $R^3$, $R^4$, $R^6$, $R^7$, and $R^8$ are independently hydrogen or alkyl.

11. The compound of claim 7, wherein $R^3$, $R^4$, $R^6$, $R^7$, and $R^8$ are hydrogen.

12. The compound of claim 1, wherein $R^1$, $R^2$, $R^3$, $R^4$, $R^6$, $R^7$ and $R^8$ and A are optionally substituted with $^2$H (deuterium).

13. The compound of claim 1, wherein the compound is in the form of a hydrochloride salt.

14. The compound of claim 1, wherein the compound is enantiomerically pure and/or diastereomerically pure.

15. A pharmaceutical composition comprising the compound of claim 1, and a pharmaceutically acceptable carrier, excipient, or diluent.

16. A method of treating psychosis, schizophrenia, acute mania, bipolar disorder, autistic disorder or depression, the method comprising administering to a patient in need thereof the pharmaceutical formulation claim 15.

17. The method of claim 16, wherein said method treats depression.

18. The method of claim 16, wherein said method treats schizophrenia.

19. The method of claim 16, wherein said method treats psychosis.

20. The method of claim 16, wherein said method treats autistic disorder.

* * * * *